United States Patent [19]

Hasegawa

[11] 4,273,531
[45] Jun. 16, 1981

[54] ROOT CANAL MEASURING APPARATUS

[76] Inventor: Kiyoshi Hasegawa, 2-11-10, Hirata, Ichikawa-shi, Chiba-ken, Japan

[21] Appl. No.: 37,293

[22] Filed: May 9, 1979

[30] Foreign Application Priority Data

May 15, 1978 [JP] Japan ................................ 53/57304

[51] Int. Cl.³ ........................................... A61C 19/04
[52] U.S. Cl. ...................................... 433/27; 128/734
[58] Field of Search ............. 128/741, 734, 735, 422, 128/776, 787, 2 N, 2.1 R, 2.12; 433/27, 28; 33/174 D

[56] References Cited

U.S. PATENT DOCUMENTS

| | | | |
|---|---|---|---|
| 3,866,600 | 2/1975 | Rey | 128/734 |
| 3,894,532 | 7/1975 | Morey | 128/734 |
| 3,901,216 | 8/1975 | Felger | 433/27 |
| 3,916,529 | 11/1975 | Moussew | 128/734 |
| 3,993,044 | 11/1976 | McGuffin | 433/27 |
| 4,177,799 | 12/1979 | Masreliez | 433/24 |

Primary Examiner—Robert Peshock

[57] ABSTRACT

A root canal measuring apparatus can measure a length of a root canal without using an oral electrode. The apparatus is composed of an oscillating circuit having a relatively high output impedance, an output terminal connected to one output end of the oscillating circuit and also connected to a tooth electrode, another output terminal connected to the other output end of the oscillating circuit and also connected to a conductive portion forming an electrostatic capacity with a patient, and a display unit for displaying a variation in voltage between both the output terminals.

9 Claims, 8 Drawing Figures

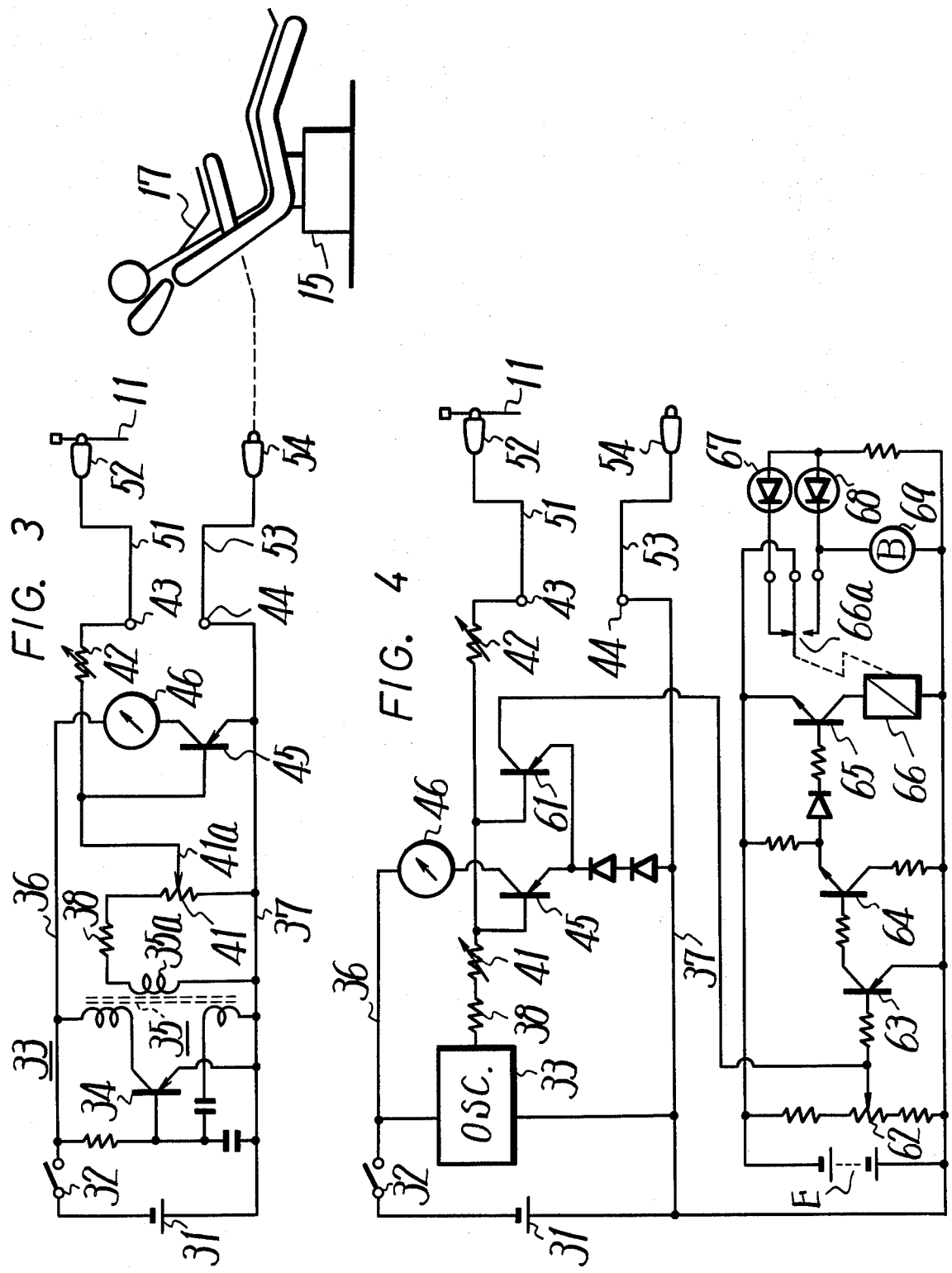

ROOT CANAL MEASURING APPARATUS

BACKGROUND OF THE INVENTION

1. Field of the Invention

This invention relates mainly to a root canal measuring apparatus, and more particularly to an improved root canal measuring apparatus using a tooth electrode only.

2. Description of the Prior Art

In root canal treatments, it is required to correctly know the length of a root canal, or the length from the incisal edge of a tooth or the edge of a tooth cavity through the root canal to the stricture portion of the root apex (hereinafter referred to as a root canal length).

FIG. 1 is a schematic cross-sectional view showing a construction of a tooth, in which reference numeral 1 designates a tooth, 2 a pulp, 3 a root canal in which the pulp 2 is housed and 4 a cavity bored in the tooth material reaching the root canal 3. Further, 5 denotes a alveolar bone, 6 a gingiva, and 7 a root canal membrane.

For example, in the root canal treatment, the root canal 3 surrounded by a necrosis dentin has no spontaneous protective force or spontaneous treatment capacity, and hence treatments of removing damages in periodontal tissue, such as the removal of infected part or protection of re-infection, are required, or root canal widening or root canal filling treatments become necessary. In this case, however, the treatments of periodontal tissue such as the periodontal membrane 7 spaced from the apical stricture portion 3A at the apex of the root canal 3 are not desirable because the above treatments result in the obstruction of the spontaneous protective force or spontaneous treatment capacity present in the periodontal tissue.

Further, in extirpation of the pulp, the pulp 2 is desired to be cut at the apical stricture portion 3A in which the circulation of blood necessary for hurt treatment can be expected from a viewpoint of the hurt treatment after the extirpation of pulp. For this reason, it is required to measure the position of the apical stricture portion 3A, or the root canal length 1.

As described above, in the dental treatment, the measurement of the root canal length 1 is indispensable. As a prior art measuring method of root canal lengths, there have been proposed a measuring method using X-ray photography, a method of measuring root canal length by feeling of operator's fingers or patient's complain of pain when the tip of a needle inserted into the root canal 3 has reached the apical stricture portion 3A, and the like. However, when using the X-ray photography, it is difficult to correctly arrange an X-ray film at a predetermined position inside a narrow mouth. For the above reason, it is quite difficult to achieve a correct measurement of the root canal length. Also, its operation is complicated, and an influence of X-ray onto a human body will come into question. Further, in the case of using the feeling of operator's fingers and the patient's complain of pain, their experiences are individually different in a great range and hence correct measurements of root canal length are carried out with difficulty.

In order to remove the above defects, a method of electrically measuring root canal length has recently been proposed and spotlighted. This apparatus utilizes characteristics such that an electric resistance between an oral mucous membrane 9 and a periodontal membrane 7 always exhibits a constant value at any portion of the periodontal membrane 7 as mentioned previously. It is experimentally noticed that this resistance value is about 6 to 6.5 KΩ which is quite lower than a resistance value of the tooth 1 itself. This apparatus is constructed as shown in FIG. 2 by way of example.

In FIG. 2, a tooth electrode, for example, a reamer 11 is connected through a clip 25 and a current detecting resistor 22 to one end of an oscillating circuit 21 of a low frequency, for example, 50 to 3000 Hz, while a saliva removing pipe 12 serving as an oral mucous membrane electrode is connected through a clip 26 to the other end of the oscillating circuit 21. An amplifier 23 is connected across the resistor 22 and the output end of the amplifier 23 is connected to a meter 24.

With the above mentioned apparatus shown in FIG. 2, when the reamer 11 is inserted into the root canal 3 but its tip is not reached to the periodontal membrane 7, a resistance between the reamer 11 and the saliva removing pipe 12 is relatively large and a current flowing through the resistor 22 is small, so that the meter 24 shows a small deflection. However, as the tip of the reamer 11 approaches the periodontal membrane 7, the deflection of the meter 24 becomes gradually large. When the tip of the reamer 11 has reached the periodontal membrane 7, the resistance between the reamer 11 and the pipe 12 becomes a substantially constant value in a range from 6 to 6.5 KΩ and the deflection of the meter 24 becomes large. For example, when the full scale of the meter 24 is selected as 50 μA, the pointer of the meter 24 will indicate a value in a range from 40 to 42 μA.

Accordingly, in order to measure the root canal length 1, the reamer 11 is first gently inserted into the root canal 3. Then, when the meter 24 shows a constant value, it means that the tip of the reamer 11 has reached the periodontal membrane 7. Therefore, at that time the reamer 11 is put thereon with a proper mark before the reamer 11 is drawn out. Thereafter, the length of the reamer 11 between the tip and the mark is measured to obtain the root canal length 1 necessary for treatment. In a practical case, however, zero-point adjustment and full-scale adjustment of the meter 24 are required to be carried out before measuring.

Thus, according to this measuring apparatus, the root canal length 1 can be simply and precisely measured. However, the apparatus is required to use the oral mucous membrane electrode, or the saliva removing pipe 12, and hence the root canal length 1 can not be measured without using the above pipe 12. In addition, the pipe 12 must be made of metal as an electrode in this case. Recently, however, saliva removing pipes made of resin such as vinyl are being pervaded due to flexibility, light weight, easiness in use, and the like. Accordingly, with the prior art apparatus, when the saliva removing pipe made of resin is used, additional oral mucous membrane electrode made of metal must be inserted in the mouth, so that an operating space becomes narrow and the additional electrode acts to obstruct the operation. Further, even in the case of using the saliva removing pipe made of metal, the clip 26 must be connected to the pipe and hence it causes inconvenience in handling.

SUMMARY OF THE INVENTION

Accordingly, it is an object of this invention to provide a root canal measuring apparatus which can measure the root canal length 1 by using only one tooth electrode without using an oral mucous membrane electrode, or a saliva removing pipe.

It is another object of this invention to provide a root canal measuring apparatus which can measure the root canal length precisely with no individual difference.

It is a further another object of this invention to provide a root canal measuring apparatus which uses an electrostatic capacity between a patient and a dental chair in order to form a measuring circuit.

It is a still further object of this invention to provide a root canal measuring apparatus whose measuring sensibility can be enhanced with a simple construction.

It is an additional object of this invention to provide a root canal measuring apparatus which utilizes a quite small current for measurement to prevent a patient from being attacked by an electrical shock or the like.

According to the main feature of this invention, there is provided a root canal measuring apparatus, which includes an oscillating circuit having a relatively high output impedance, an output terminal connected to one output end of the oscillating circuit and also connected to a tooth electrode, another output terminal connected to the other output end of the oscillating circuit and also connected to the other electrode, and display means for displaying a variation in voltage between both of the output terminals.

The other objects, features and advantages of this invention will be apparent from the following description taken in conjunction with the accompanying drawings.

BRIEF DESCRIPTION OF THE DRAWINGS

FIG. 3 is a connection diagram showing one embodiment of a root canal measuring apparatus according to this invention, FIG. 4 is a connection diagram showing another embodiment of the root canal measuring apparatus of this invention.

DESCRIPTION OF THE PREFERRED EMBODIMENTS

Figure 1:
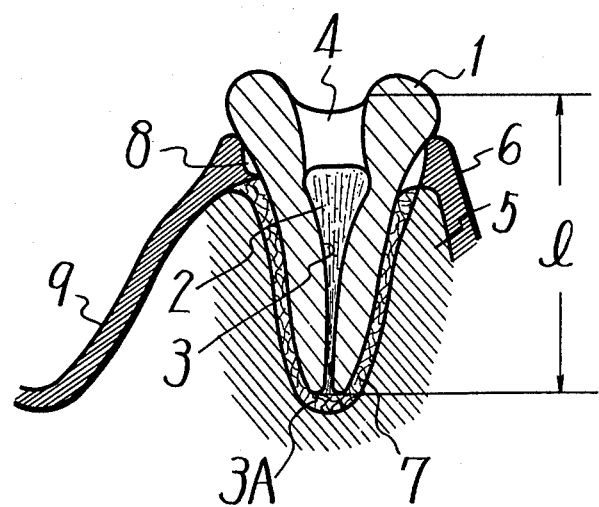
FIG. 1 is a schematic view showing a construction of a tooth used for explaining this invention.

A description will hereinafter be given on one embodiment of this invention with reference to FIG. 3.

In FIG. 3, a DC power source 31, for example, a dry cell of 1.5 volts, is connected through a switch 32 to an oscillating circuit generally indicated by 33. The oscillating circuit 33 consists of a transistor 34, an oscillating transformer 35 and the like, and is connected between a power source line 36 and a ground line 37. As an oscillating output of the circuit 33, a feeble alternating voltage having a high frequency of, for example, several hundred KHz is derived from an output winding 35a of the transformer 35.

The output winding 35a of the transformer 35 is connected at its one end through a resistor 38 to a potentiometer 41 and at its other end to the ground line 37. A movable contact 41a of the potentiometer 41 is connected through a variable resistor 42 to an output terminal 43. The movable contact 41a of the potentiometer 41 is also connected to the base of a transistor 45. The collector of the transistor 45 is connected through a meter 46 to the power line 36, and the emitter thereof is connected to the ground line 37, which is also connected to other output terminal 44.

The terminal 43 is connected through a cord 51 to a clip 52 which is fastened to a reamer 11 while the other terminal 44 is connected through a cord 53 to a clip 54. The clip 54 is coupled to a conductive portion of a dental unit (not shown) which is electrically connected to a dental chair 15.

With such an arrangement, an apparent output impedance of the oscillating circuit 33 viewing from the movable contact 41a of the potentiometer 41 becomes relatively high according to an output impedance of the oscillating circuit 33 itself and the resistances of the resistors 38 and 41. Thus, when a patient 17 sits on the chair 15, equivalently the patient 17 is coupled to the chair or conductive portion 15 through an electrostatic capacity therebetween and hence the clip 54 is electrically connected to the oral mucous membrane 9 (refer to FIG. 1) of the patient 17 through the electrostatic capacity.

Meanwhile, when the switch 32 is closed, the oscillating circuit 33 produces an alternating voltage which is obtained at the movable contact 41a of the potentiometer 41. In the case that the tip of the reamer 11 has not yet reached the periodontal membrane 7, the voltage obtained at the movable contact 41a of the potentiometer 41 is supplied, as it is, to the transistor 45 where it is rectified and also amplified before being fed to the meter 46. As a result, the meter 46 shows the maximum deflection.

Figure 2:
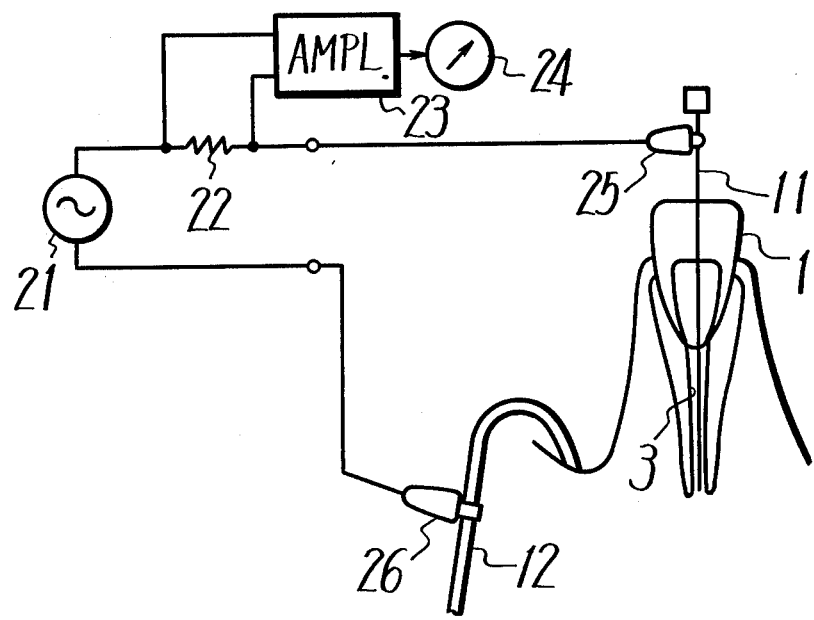
FIG. 2 is a connection diagram showing one example of a prior art root canal measuring apparatus.

However, when the tip of the reamer 11 has reached the periodontal membrane 7, since the oral mucous membrane 9 of the patient 17 is connected through the electrostatic capacity to the clip 54, an alternating current (an oscillating signal) flows through these elements. If the current flows therethrough, a voltage drop occurs according to the impedance of the oscillating circuit 33 from the movable contact 41a of the potentiometer 41. Therefore, the voltage at the movable contact 41a is lowered and hence the deflection of the meter 46 becomes small. In other words, with the prior art apparatus shown in FIG. 2, the variation in measured current is displayed by the meter 24, while with this invention, the variation in voltage is displayed by the meter 46.

With the above mentioned apparatus, the root canal length l is measured in the following manner.

At first, with the switch 32 being closed, the potentiometer 41 is adjusted to make the meter 46 in a condition of full scale, for example, 50 μA. At this time, the reamer 11 is kept isolated from any portion. Next, with the reamer 11 being brought into contact with the oral mucous membrane 9, the variable resistor 42 is adjusted to make the meter 46 zero in reading. Accordingly, with the above adjustment, the meter 46 is calibrated, and even though an impedance exists between the clip 54 and the oral mucous membrane 9, this impedance will be negligible. If necessary, these full-scale adjustment and zero-point adjustment are repeated once or twice for confirmation. In this case, if a condition of using the dental chair 15 and the like is kept unchanged, the zero-point adjustment is made once and thereafter it can be omitted.

Then, the reamer 11 is gently inserted into the root canal 3 of the tooth 1 to be treated. In this case, unless the tip of the reamer 11 reaches the periodontal membrane 7, almost no current flows through the reamer 11 and hence the meter 46 remains full in scale. However, according as the tip of the reamer 11 approaches the periodontal membrane 7, a current flows through the reamer 11 to lower the voltage at the movable contact 41a of the potentiometer 41 and hence the deflection of the meter 46 is being reduced. Then, when the tip of the reamer 11 reaches the membrane 7, the electric resistance between the reamer 11 and the oral mucous membrane 9 always exhibits nearly the same and stable value, therefore the deflection of the meter 46 also becomes constant and stable. For example, when the full scale of the meter 46 is 50 $\mu$A, the meter 46 is stabilized at a scale in a range of 8 to 10 $\mu$A. Accordingly, when the deflection of the meter 46 is stabilized at a constant value, the reamer 11 is extracted from the root canal 3 with a mark being put thereon, and the length of the reamer 11 between the mark and the tip is measured to obtain the length of root canal 1.

In this case, after the calibration of the meter 46 has been finished, the reamer 11 is inserted into a periodontal pocket 8 at the interdental papilla of the tooth to be treated to read the deflection of the meter 46 when the reamer 11 reaches the bottom of the periodontal pocket 8. This reading will be equivalent to the reading of the meter 46 when the reamer 11 reaches the periodontal membrane 7 at the apical structure 3A due to the fact that an electric resistance between the oral mucous membrane 9 and the periodontal membrane 7 always shows a constant value at any portion of the periodontal membrane 7 as described previously. For this reason, more precise measurements with no individual difference can be always attained.

Thus, according to this invention, the root canal length 1 can be measured without using an oral electrode or the saliva removing pipe 12 so that an operable area is widened with no obstacle. Also, even in case of requiring the saliva removing pipe 12, a pipe made of any material such as resin, metal or the like can be used arbitrarily and further the root canal length 1 can be measured freely. Even though the saliva removing pipe 12 made of metal is used, a clip is not necessary for connection so that the saliva removing pipe 12 can be easily handled.

Further, according to this invention, the electrostatic capacity between the chair 15 and the patient 17 is utilized to make an equivalent connection between the terminal 44 and the oral mucous membrane 9 of the patient 17, so that as compared with the case of using the metallic saliva removing pipe 12 there is no error caused by incomplete contact or the like and stable measurements can be achieved. In addition, the output impedance of the oscillating circuit 33 viewing from the movable contact 41a of the potentiometer 41 is utilized to obtain a variation in voltage at the movable contact 41a thereby detecting whether the reamer 11 has reached the periodontal membrane 7 or not, so that the detecting sensibility can be enhanced with a simple construction. There is also such an advantage that when measuring, a current flowing through the reamer 11 can be limited as little as possible so that a trouble such as electric shock to the patient 17 may not occur. According to practical measurements, a current flowing through the periodontal tissue was less than 1 $\mu$A even when the reamer 11 has reached the periodonal membrane 7.

Moreover, since the circuit arrangement is simple, its miniaturization and weight lightening can be achieved with the cost being reduced, and other operating instruments will not be obstructed thereby. Besides, the apparatus of this invention is simple in handling and excellent in performance. In addition, since its current consumption is small, the dry cell 31 of 1.5 V can be used for a long time period or a small capacity of dry cell can be used. Also, operators and patients are not harmed as in the case of X-ray taking method, and measurement results can be known immediately.

FIG. 4 shows another embodiment of this invention, in which the arrival of the reamer 11 at the periodontal membrane 7 is displayed by a luminescent element and/or a buzzer as well as the reading of the meter 46. In FIG. 4, elements corresponding to those of FIG. 3 will be indicated by the same reference numerals with their description being omitted.

In addition to the circuit of FIG. 3, there is provided a transistor 61 whose emitter is connected to the emitter of the transistor 45 and whose base is connected to the base of the transistor 45. The collector of the transistor 61 is connected to a sensibility adjusting potentiometer 62 at its moval contact, while another DC power source E is connected across the potentiometer 62. The movable contact of the potentiometer 62 is also connected to the base of a transistor 63 which is connected in cascade to a transistor 64. The emitter of the transistor 64 is connected through a diode and a resistor to the base of a transistor 65, while the emitter of the transistor 65 is connected to the negative electrode of the DC power source E and the collector thereof is connected through a relay 66 to the positive electrode of the power source E. There is provided a relay switch 66a in association with the relay 66. The movable contact of the switch 66a is connected to the emitter of the transistor 65, while one fixed contact thereof is connected to the cathode of a light emitting diode (LED) 67 and the other fixed contact thereof is connected to the cathode of other LED 68 and also through a buzzer 69 to the positive electrode of the power source E. The anodes of the LEDs 67 and 78 are connected in common to the positive electrode of the power source E.

With such a circuit arrangement, a voltage supplied to the transistor 45 is partially taken out by the transistor 61, and thus taken-out voltage is fed to the sensibility adjusting potentiometer 62 and also through the transistors 63, 64 and 65 to the relay 66. In this case, when the tip of the reamer 11 is not yet reached to the periodontal membrane 7, the relay 66 is in its off state and the cathode of the LED 67 is connected to the movable contact of the relay switch 66a so that a circuit for driving the LED 67 by the power source E is closed to turn the LED 67 on. On the other hand, when the tip of the reamer 11 has reached the periodontal membrane 7, the relay 66 is turned on and also the movable contact of its switch 66a is changed over to the cathode side of the LED 68 to close a circuit for driving the LED 68 and the buzzer 69 by the power source E so that the LED 68 is turned on and also the buzzer 69 rings to inform the operator that the tip of the reamer 11 has arrived at a predetermined position of the periodontal membrane 7.

In the above embodiments, the voltage obtained at the movable contact 41a of the potentiometer 41 is rectified and amplified by the transistor 45 before being fed to the meter 46. However, according to this invention, its sensibility is high as described above, so that the meter 46 can be driven even though the transistor 45 is not used.

Figure 5:
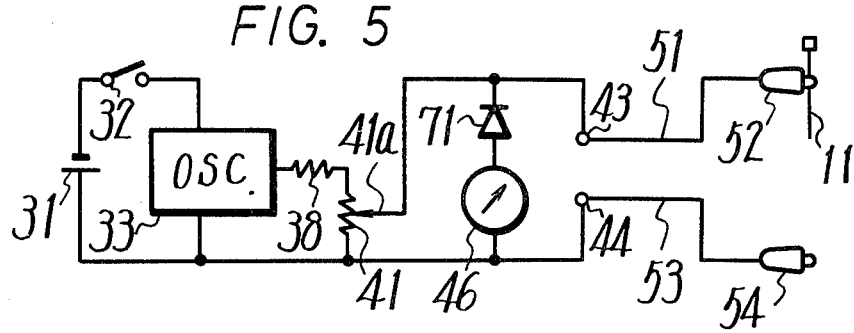
FIG. 5, FIG. 6 and FIG. 7 are connection diagrams each showing a further another embodiment of this invention.
Figure 6:
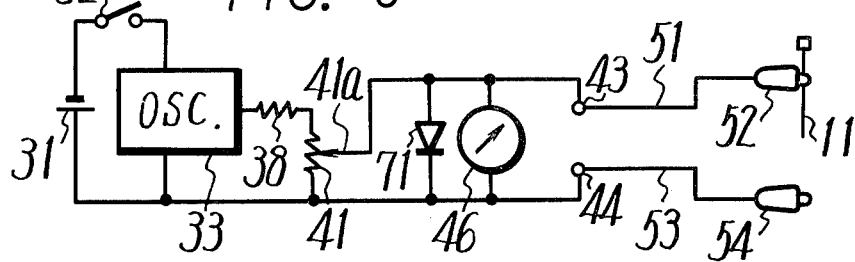
Figure 7:
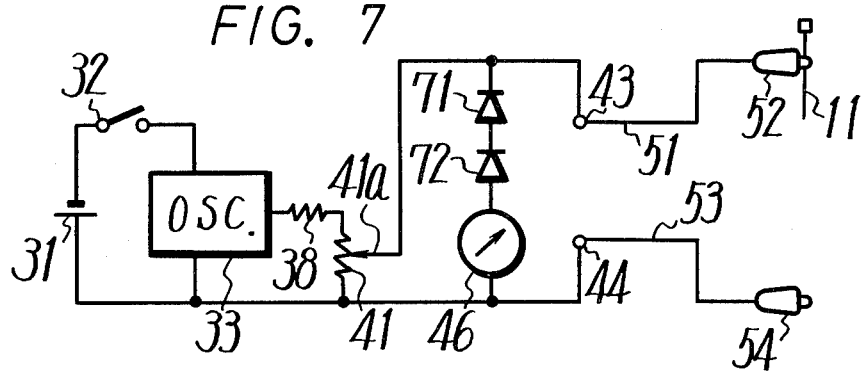

To this end, embodiments shown in FIGS. 5 and 6 are respectively proposed, in which a diode 71 is used for rectifying purpose. FIG. 7 shows another embodiment of this invention, in which a diode 72 is further added to the example shown in FIG. 5. With such an arrangement, the sensibility of the meter 46 is improved according to a forward drop voltage of the diode 72 similarly as in the embodiment of FIG. 4 in which the emitter of the transistor 45 is connected through series-connected diodes to the positive electrode of the dry cell 31.

Figure 8:
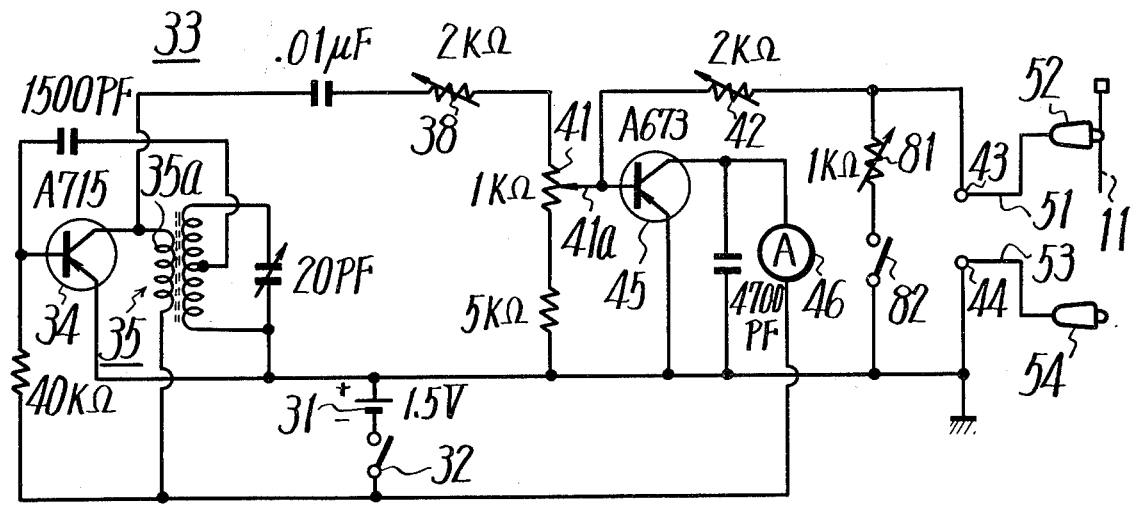
FIG. 8 is a connection diagram showing a practical embodiment of the root canal measuring apparatus according to this invention.

FIG. 8 shows an improved embodiment of this invention, in which values of respective elements are practically indicated by way of example. The frequency of this oscillating circuit 33 is selected to be about 1.7 to 2.0 MHz in order to avoid noise generation caused by the radio frequency and to enhance the sensibility of this circuit. In FIG. 8, a variable resistor 81 and a switch 82 are provided between both the terminals 43 and 44 for adjusting the meter 46 when assembling the apparatus. In this example, the resistor 38 is made variable which is also used to adjust the oscillating output of the oscillating circuit 33 upon assembling the apparatus, and the variable resistor 42 is used to adjust the meter 46 upon assembling the apparatus. In adjusting the meter 46, with the switch 32 being turned on, the variable contact 41a of the potentiometer 41 is adjusted to ascertain whether the meter 46 operates or not thereby to check the capacity of the dry cell 31. Next, with a switch 82 being turn on, the variable contact 41a of the potentiometer 41 is adjusted to bring a pointer of the meter 46 to a position of, for example, 10 μA.

Further, in the above described embodiments, the clip 54 or the cord 53 is coupled to the chair 15, but it is also possible to couple the former to the dental unit or to a conductive member enclosed in a cushion. In other words, the terminal 44 is required to be electrically connected to the patient 17 through, for example, an electrostatic capacity.

It will be apparent that many modifications and variations may be effected without departing from the scope of the novel concepts of this invention.

I claim as my invention:

1. A root canal measuring apparatus comprising:
 a DC power source having positive and negative terminals;
 an oscillating circuit having a relatively high output impedance and connected at one output end to the negative terminal of said power source and at its other output end to the positive terminal thereof, said oscillating circuit producing a high frequency output;
 a first output terminal leading from one output end of said oscillating circuit;
 a second output terminal leading from the other output end of said oscillating circuit;
 a first electrode connected to said first output terminal of said oscillating circuit, said first electrode comprising a probe insertable through a root canal of a patient to his periodontal membrane whose root canal length is to be measured;
 a support for said patient including a conductive portion which forms with the patient an electrostatic capacitor; and
 coupling means connecting said second output terminal and said support;
 means for detecting variations in voltage between said first and second output terminals; and
 display means responsive to the detection of voltage.

2. A root canal measuring apparatus according to claim 1, wherein said power source is a dry cell of 1.5 volts.

3. A root canal measuring apparatus according to claim 2, wherein said oscillating circuit includes, at least, a transistor and an oscillating transformer.

4. A root canal measuring apparatus according to claim 3, wherein said display means is an ammeter and cooperates with a transistor.

5. A root canal measuring apparatus according to claim 3, wherein said display means is an ammeter and cooperates with a diode.

6. A root canal measuring apparatus according to claim 1, wherein adjusting means is a potentiometer.

7. A root canal measuring apparatus according to claim 6, including means responsive to variations in voltage for detecting the position of said probe relative to the periodontal membrane comprising a relay with a relay switch, a first and second light-emitting devices, and a buzzer, said first light-emitting device acting to indicate that said probe has not reached the periodontal membrane of said patient, and said second light-emitting device and said buzzer acting to indicate the arrival of said probe to the periodontal membrance of said patient.

8. A root canal measuring apparatus according to claim 7, further including another DC power source for driving said first and second light-emitting devices and said buzzer, and another potentiometer for sensibility adjustment.

9. A root canal measuring apparatus according to claim 1, wherein said oscillating circuit produces a high frequency output of at least several hundred KH$_z$.

* * * * *